United States Patent [19]

Boie et al.

[11] 4,138,263

[45] Feb. 6, 1979

[54] PHOTOGRAPHIC SILVER HALIDE MATERIAL WITH 2-EQUIVALENT, N-HETEROCYCLIC YELLOW COUPLERS

[75] Inventors: Immo Boie; Günter Renner, both of Cologne; Friedrich-Wilhelm Kunitz, Leverkusen, all of Fed. Rep. of Germany

[73] Assignee: Agfa-Gevaert Aktiengesellschaft, Fed. Rep. of Germany

[21] Appl. No.: 604,312

[22] Filed: Aug. 13, 1975

Related U.S. Application Data

[63] Continuation-in-part of Ser. No. 532,904, Dec. 16, 1974, abandoned.

[30] Foreign Application Priority Data

Dec. 21, 1973 [DE] Fed. Rep. of Germany ....... 2363675

[51] Int. Cl.² .......................... G03C 1/40; G03C 7/00
[52] U.S. Cl. .................................. 96/100 N; 96/56.5
[58] Field of Search ..................... 96/100, 56.5, 100 N

[56] References Cited

U.S. PATENT DOCUMENTS

3,900,483   8/1975   Fujimatsu et al. ..................... 96/100

FOREIGN PATENT DOCUMENTS

2169879   9/1973   France ....................................... 96/100
2318807  10/1973   Fed. Rep. of Germany ............ 96/100

*Primary Examiner*—Richard L. Schilling
*Attorney, Agent, or Firm*—Connolly and Hutz

[57] ABSTRACT

2-Equivalent yellow couplers for the production of yellow dye images in color photographic silver halide materials have as splittable group a nitrogen-containing 6-membered heteroaromatic ring which is linked by the said nitrogen atom to the coupling position of the coupler molecule, contains a carbonyl group adjacent said nitrogen, and also contains one or two additional nitrogens as well as a fused-on aromatic carbocyclic ring. When the heteroaromatic ring contains two additional nitrogens, all three nitrogens are vicinal; when it contains only one additional nitrogen, the splittable group is a 1,3-quinazolinone-4 having at least one carboxy, with lower aliphatic alcohols esterified carboxy, nitro, methyl or chloro substituent.

9 Claims, No Drawings

PHOTOGRAPHIC SILVER HALIDE MATERIAL WITH 2-EQUIVALENT, N-HETEROCYCLIC YELLOW COUPLERS

This application is a continuation-in-part of application Ser. No. 532,904 filed Dec. 16, 1974 and subsequently abandoned.

This invention relates to new 2-equivalent yellow couplers and their use for the production of yellow dye images in color photographic silver halide materials.

In the production of color photographic images, it is usual to develop the exposed silver halide in a light-sensitive silver halide emulsion layer with an aromatic developer containing primary amine groups. The color couplers react with the oxidized color developer to form an image dye corresponding to the silver image.

In substractive three-color photography a light-sensitive multi-layer material is generally used containing a red-sensitized, a green-sensitized, and a blue-sensitized silver halide emulsion layer. When these are developed, using suitable couplers, they give a cyan, magenta and yellow image respectively.

The couplers used to form the cyan dye are generally phenols or naphthols, those producing magenta are usually pyrazolones and those producing yellow are generally compounds containing a methylene group with two carbonyl groups attached thereto. The dyes formed by coupling are azomethines, indamines or indophenols, according to the coupler and the developer used.

The conventional yellow couplers contain an active methylene group which reacts during development with oxidized color developer, four equivalents of developable silver halide being required for one equivalent of dye formed by the coupling reaction. These couplers are therefore called 4-equivalent couplers. Other known couplers, such as those disclosed in German Offenlegungsschrift 2,318,807, contain a methylene group in which one hydrogen atom is replaced by a substituent which splits off during the coupling reaction. In the latter case only two equivalents of developable silver halide form the same one equivalent of dye. For this reason these couplers are called 2-equivalent couplers. Inasmuch as the amount of silver halide required to form a specific amount of dye is about half as much with 2-equivalent couplers as is required using 4-euivalent couplers, less silver halide is required to produce the light-sensitive photographic material. As a result, the layer of emulsion can be thinner, which in turn has an advantageous effect on the resolution and sharpness of the photographic material.

Among the 2-equivalent yellow couplers known in the art those having a halogen as splittable substituent have proved to be sufficiently reactive to guarantee sufficient color densities even with short developing processes.

In practice, however, 2-equivalent yellow couplers with chlorine as the splittable substituent frequently have an adverse effect on the photographic properties of the silver halide emulsion. As described in British Patent Specification No. 1 351 395, only certain yellow couplers of the benzoyl acetanilide type with chlorine as the splittable substituent are relatively inert on storage and influence the formation of colored fog during development only slightly. Nevertheless, even these couplers do not satisfy photographic requirements in every respect, since an increase in fog formation during development cannot be completely excluded when unprocessed photographic material containing these couplers is stored in moist and warm conditions.

There has been no lack of practical attempts to find new 2-equivalent yellow couplers which should be storage stable, easily accessible for preparative purpose, and whose reactivity in the development of color photographs should be sufficient or at least comparable with presently used couplers.

One further problem, not yet completely solved in practice, is the fact that the couplers must be dispersed in the hydrophilic colloidal layers of the photographic material in a very finely divided form, either in the form of fine microcrystals or ultrafine liquid droplets and the dispersion formed should remain stable so that neither recrystallizing of the coupler should occur nor should the photographic or mechanical properties of the layers be influenced in any adverse way.

If photographic material is stored for some length of time, the 2-equivalent couplers should be sufficiently stable, particularly in moist and warm conditions, to avoid separation of the splittable group before color development takes place. On the other hand, the splittable group should be easily and completely separated during the developing process, in order to attain a high concentration of dye in the images as well as provide adequate sensitivity. These properties must, of course, be independent of the method used for the addition of the couplers to the hydrophilic colloidal layers.

Non-diffusing hydrophobic couplers are usually first dissolved, as by the use of solubilizing groups, in alkaline solution, or by the use of an organic solvent, and are then emulsified with the gelatin solution in the usual manner, generally with the addition of an oily coupler solvent. In the case of the alkali soluble couplers a gelatin solution containing such a coupler is normally neutralized, and in the case of the couplers soluble in organic solution the organic solvent is partly or totally evaporated so that the dispersed coupler remains in finely divided form in the gelatin. To obtain a sufficient reactivity of 2-equivalent couplers, the hydrophilic coupler-containing layer and/or the hydrophobic drop of oil in which the coupler is dissolved, must be able to favorably influence as by solvation, the separation of the splittable substituent during color development.

The splittable substituent, of course, should be photographically essentially inert and should not have any deleterious influence on the dyes formed on development or on the stability of the unreacted color coupler remaining in the layer.

The compounds described in U.S. Pat. No. 3,617,291 are not satisfactory in practice, since their stability in unprocessed photographic materials is inadequate when exposed to moist warm air.

The German Offenlegungsschrift No. 2 329 587 suggests the use of 2-equivalent yellow couplers which are easily prepared and which have as splittable group a 5-membered heterocyclic group containing nitrogen which heterocyclic group has a C=C double bond adjacent to the nitrogen atom, which is linked to the carbon atom of the active methylene group of the yellow coupler. Imidazoles are the preferred splittable groups, preferably containing electro-negative substituents.

The last-mentioned couplers are superior as regards both production and stability during storage, to those described in the U.S. Pat. No. 3,617,291. However, their preparation is not without problems. For instance, more reaction steps are required for the production of desirable imidazole couplers, than for other 2-equivalent couplers. Moreover, nitro-imidazole couplers for instance tend to be yellow in color even before coupling and can therefore give rise to color distortions.

Among the objects of the present invention is the provision of new 2-equivalent yellow couplers, which can easily be prepared and which are excellently suitable for use in light-sensitive color photographic materials to produce the yellow partial images and whose photographic properties are superior.

It now has been found that particularly suitable 2-equivalent yellow couplers have a splittable groups a nitrogen-containing 6-membered heteroaromatic ring which is linked by the said nitrogen atom to the coupling position of the coupler molecule, contains a carbonyl group adjacent said nitrogen, and also contains one or two additional nitrogens as well as a fused-on aromatic carbocyclic ring. When the heteroaromatic ring contains two additional nitrogens, all three nitrogens are vicinal; when it contains only one additional nitrogen, the splittable group is a 1,3-quinazolinone-4 having at least one carboxy, which may be esterified with lower aliphatic alcohols, nitro, methyl or chloro substituent.

Thus according to the present invention the splittable groups are 1,2,3-benzotriazinones which may be substituted, or carboxy, alkoxycarbonyl, alkoxy having up to 5 carbon atoms, nitro, methyl- or chloro-substituted 1,3-quinazolinones-4.

The heterocyclic compound can easily have its appropriate nitrogen attached to the coupling position of a 2-equivalent yellow coupler by known means, as by reacting the corresponding 2-equivalent yellow coupler having chlorine as splittable substituent, with a salt of said heterocyclic compound. The production of the salt of the of the said heterocyclic compound is effected as described in German Offenlegungsschrift No. 2,329,587.

In the heterocyclic splittable groups of the present invention the nitrogen atom adjoining the carbonyl group is sufficiently electron-deficient to form the corresponding salts with bases, and sufficiently nucleophilic to effect a smooth substitution with the halogen atom of a halogen-substituted active methylene group of a yellow coupler. The polar character of the splittable group also has a marked effect on the reaction speed of the couplers of the present invention with the oxidized color developer. Polar substitutions, such as with hydroxyl, nitro, carbonyl-containing or acid substituents, on the splittable group promote the reaction speed of the coupler with the oxidized color developer but can cause instability of the coupler during storage. The yellow couplers of the present invention are not only very easy to produce, but are also particularly stable during storage, even in extreme storage conditions; in addition they are extremely reactive during chromogenic development and their heterocyclic group is easily split off. Their sensitivity and color yield are outstanding. Moreover, the splittable groups of the yellow couplers of the present invention, in comparison with corresponding 4-equivalent yellow couplers, have no adverse effects on the absorptive characteristics of the dyes produced. Neither the unreacted coupler remaining after processing, nor the splittable groups freed by the processing, cause any undesired shift of the light absorption.

The 2-equivalent coupler radical which forms a yellow color in accordance with the present invention is derived from the usual known 4-equivalent couplers. Couplers suitable for the present invention are open-chain ketomethylene yellow couplers e.g. acylacetonitrile or acylacetyl coupler, in particular those having the following formula (I):

where
B represents an alkyl radical with 1–32 C-atoms, preferably 1–18 C-atoms, branched or unbranched; in the case of a secondary or tertiary alkyl radical the secondary or tertiary carbon atom should preferably be linked directly with the carbonyl radical; or an alkoxyalkyl radical, a dicycloalkyl radical, a heterocyclic radical or an aryl radical, especially a phenyl radical which may, if necessary, be substituted once or several times by alkyl with 1–18 C-atoms, aryl, aralkyl alkoxy with 1–18 C-atoms, aroxy, halogen (e.g. fluorine or bromine), acyl, acyloxy, acylamino, amino-, carbamyl- or sulfamyl groups which may be substituted by identical or different arylaralkyl, alkyl or heterocyclic radicals, sulfo or carboxy;
B' represents cyano or the group

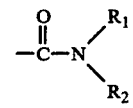

$R_1$ represents hydrogen or a short-chain alkyl radical with 1–5 C-atoms, for example a methyl or ethyl radical and
$R_2$ represents an alkyl radical with 1–18 C-atoms or preferably an aryl radical, for example a phenyl radical which may be substituted by identical or different groups such as alkyl with 1–18 C-atoms, aryl, aralkyl, aroxy, halogen (e.g. fluorine or bromine), acyl, acyloxy, acylamino, amino, carbamyl or sulfamyl groups which may be substituted by identical or different aryl, aralkyl, alkyl or heterocyclic radicals, sulfo or carboxy.

Preferred coupler radicals are those which are derived from 4-equivalent yellow couplers which produce dyes having the desired absorption and stability required in practice. Benzoylacetanilides in particular o-alkoxybenzoylacetanilides and pivaloylacetanilides which may be substituted in the anilid group of the coupler molecule by one or several optionally one to three substituents preferably in the 2-, 4- and 5-position of the anilid group, are shown to be of preferred practical importance.

The yellow couplers of the present invention are extremely suitable for use in light-sensitive silver halide emulsion layers of single or multi-layered color photographic materials.

It is not necessary for the yellow couplers to be incorporated into the light-sensitive layers; it is also possible to accommodate them in a layer of binder adjacent to the blue sensitive light-sensitive silver halide emulsion layer.

The yellow couplers of the present invention can be used as diffusionfast or non-diffusionfast forms, by a suitable choice of substituents. To obtain a sufficient degree of diffusionfastness, substituents $R_1$, $R_2$ or B are provided with radicals which prevent diffusion, e.g. straight-chain or branched alkyl radicals with 10–18 C-atoms, or they can be substituted by alkyl-substituted phenoxy radicals which are bonded either directly or indirectly via —O—, —S—, —CONH—, —NHCO—, —SO$_2$NH— —NHSO$_2$— or other intermediate members of the radicals B, $R_1$ or $R_2$.

If solubility in alkali is desired, at least one of the radicals B, $R_1$ or $R_2$ may carry groups which favor this property, especially sulfo groups.

Diffusion-promoting groups are particularly suitable for couplers used in developer solutions, in order to develop the yellow dye in exposed color films which contain no yellow coupler.

Examples of suitable yellow couplers which are to be used according to the present invention are as follows:

Table 1

$$B-CO-CH(X)-CO-NH-\text{Ar}(R', R'')$$

where X = (4-oxo-benzotriazinyl)

and B, R' and R'' are as listed.

| No. | B | R' | R'' | m.p. °C |
|---|---|---|---|---|
| 1 | 2-OC$_{16}$H$_{33}$-phenyl | H | H | 143–146 |
| 2 | t-butyl | —OC$_{16}$H$_{33}$ | —SO$_2$NHCH$_3$ | 130–131 |
| 3 | t-butyl | —OC$_{16}$H$_{33}$ | —SO$_2$N(CH$_3$)$_2$ | 93–96 |
| 4 | t-butyl | Cl | —NH—CO—(CH$_2$)$_3$—O—(2,4-di-t-C$_5$H$_{11}$-phenyl) | 180 |
| 5 | 3,5-di-methoxyphenyl (CH$_3$O-, -OCH$_3$) | —OC$_{16}$H$_{33}$ | —SO$_2$NHCH$_3$ | 78–80 |
| 6 | t-butyl | Cl | —NHCOC$_{15}$H$_{31}$ | 172–173 |
| 7 | t-butyl | —OC$_{14}$H$_{29}$ | —SO$_2$NHCH$_3$ | 120 |
| 8 | t-butyl | Cl | —OC$_{14}$H$_{29}$ | 47–50 |
| 9 | t-butyl | Cl | —COOC$_{14}$H$_{29}$ | 60–63 |
| 10 | t-butyl | Cl | —COOCH(COOC$_{14}$H$_{29}$)(CH$_3$) | 45 |
| 11 | t-butyl | —OC$_{16}$H$_{33}$ | H | 98–99 |
| 12 | 2-OC$_{16}$H$_{33}$-phenyl | —OCH$_3$ | —SO$_2$—NH—(sulfolanyl) | 110–113 |
| 13 | 2-OC$_{16}$H$_{33}$-phenyl | —OCH$_3$ | —SO$_2$NHCH$_3$ | 98–99 |
| 14 | 4-CH$_3$O-phenyl | —N(CH$_3$)C$_{18}$H$_{37}$ | —SO$_2$—NH—(sulfolanyl) | 156–158 |

Table 1-continued $$B-CO-CH(X)-CO-NH-\text{Ar}(R', R'')$$

where X = (3-oxo-benzotriazin-4-yl group)

and B, R' and R'' are as listed.

| No. | B | R' | R'' | m.p. °C |
|---|---|---|---|---|
| 15 | 4-CH₃O-C₆H₄- | —N(CH₃)C₁₈H₃₇ | —SO₂NHCH₃ | 110–111 |
| 16 | 2-(OC₁₆H₃₃)-C₆H₄- | —OCH₃ | —SO₂NHC₄H₉ | 131–132 |
| 17 | 4-CH₃O-C₆H₄- | —N(CH₃)C₁₈H₃₇ | —SO₂NHC₄H₉ | 100–102 |
| 18 | 2-(OC₁₄H₂₉)-C₆H₄- | —OCH₃ | H | 99 |

Table 2

$$B-CO-CH(X)-CONH-\text{Ar}(R', R'')$$

where X = (4-chloro-quinazolin-3(4H)-on-yl group)

and again B, R' and R'' are as listed.

| No. | B | R' | R'' | m.p. °C |
|---|---|---|---|---|
| 19 | t-butyl | —OC₁₆H₃₃ | —SO₂NHCH₃ | 110–112 |
| 20 | t-butyl | —OC₁₄H₂₉ | —SO₂NHCH₃ | 96–99 |
| 21 | t-butyl | —OC₁₆H₃₃ | H | 67–68 |
| 22 | 2-(OC₁₄H₂₉)-C₆H₄- | —OCH₃ | H | 103 |

Table 2-continued
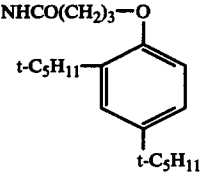
where X =
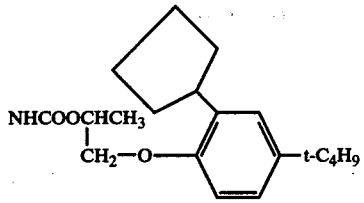
and again B, R' and R" are as listed.
| No. | B | R' | R" | m.p. °C |
|---|---|---|---|---|
| 23 | t-butyl | Cl | —NHCO(CH$_2$)$_3$—O—(2-t-C$_5$H$_{11}$, 4-t-C$_5$H$_{11}$-phenyl) | 231–234 |
| 24 | t-butyl | Cl | 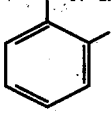 | 211 |
Table 3
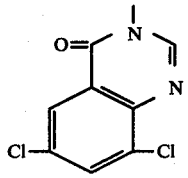
| No. | B | R' | R" | X | m.p. °C |
|---|---|---|---|---|---|
| 25 |  (OC$_{14}$H$_{29}$, o-methylphenyl) | OCH$_3$ | H |  | 53 |
| 26 | t-butyl | —OC$_{16}$H$_{33}$ | —SO$_2$NHCH$_3$ | 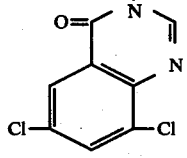 | 82–85 |
| 27 | t-butyl | —OC$_{16}$H$_{33}$ | H |  | 91 |

Table 3-continued $$B-CO-\underset{X}{CH}-CONH-\text{[phenyl with R' ortho and R'' para]}$$

| No. | B | R' | R" | X | m.p. °C |
|---|---|---|---|---|---|
| 28 | t-butyl | —OC₁₆H₃₃ | —SO₂NHCH₃ | 3-methyl-4(3H)-quinazolinon-3-yl (8-methyl) | 81–82 |
| 29 | t-butyl | —OC₁₆H₃₃ | —SO₂NHCH₃ | 5,7-dimethyl-4(3H)-quinazolinon-3-yl | 111–113 |
| 30 | t-butyl | —OC₁₄H₃₃ | —SO₂NHCH₃ | 5,7-dimethyl-4(3H)-quinazolinon-3-yl | 108–111 |
| 31 | t-butyl | —OC₁₆H₃₃ | H | 2-methyl-4(3H)-quinazolinon-3-yl | oily |
| 32 | t-butyl | —OC₁₆H₃₃ | —SO₂NHCH₃ | 7-nitro-1,2,3-benzotriazin-4(3H)-on-3-yl | 84–86 |
| 33 | t-butyl | —OC₁₆H₃₃ | —SO₂NHCH₃ | 5,7-dimethyl-1,2,3-benzotriazin-4(3H)-on-3-yl | 74–76 |
| 34 | 2,4-dimethoxyphenyl | —OC₁₈H₃₇ | —SO₂NHCH₃ | 5,7-dimethyl-4(3H)-quinazolinon-3-yl | 131–133 |

Table 3-continued $$\text{B—CO—CH(X)—CONH—Ar(R')(R'')}$$

| No. | B | R' | R'' | X | m.p. °C |
|---|---|---|---|---|---|
| 35 | t-butyl | Cl | —NH—CO—(CH₂)₃—O—C₆H₃(t-C₅H₁₁)₂ | 3-methyl-2-oxo-quinazolinyl | 204–206 |
| 36 | t-butyl | Cl | —NH—CO—(CH₂)₃—O—C₆H₃(t-C₅H₁₁)₂ | 6,8-dimethyl-2-oxo-quinazolinyl | 112–116 |
| 37 | t-butyl | Cl | —NH—CO—(CH₂)₃—O—C₆H₃(t-C₅H₁₁)₂ | 5,7-dichloro-2-oxo-quinazolinyl | 240 |
| 38 | t-butyl | —OC₁₆H₃₃ | —SO₂N(CH₃)₂ | 6,8-dimethyl-2-oxo-quinazolinyl | 116–117 |
| 39 | t-butyl | —OC₁₆H₃₃ | —SO₂NHCH₃ | 6-carboxy-2-oxo-quinazolinyl | 150–152 |
| 40 | t-butyl | —OC₁₆H₃₃ | —SO₂NHCH₃ | 6-(butoxycarbonyl)-2-oxo-tetrahydroquinazolinyl | oily |
| 41 | t-butyl | —OC₁₆H₃₃ | —SO₂NHCH₃ | 6-nitro-2-oxo-quinazolinyl | 94–96 |

Table 3-continued $$\text{B-CO-CH(X)-CONH-} \underset{R''}{\overset{R'}{\text{C}_6\text{H}_3}}$$

| No. | B | R' | R'' | X | m.p. °C |
|---|---|---|---|---|---|
| 42 | t-butyl | —OC₁₆H₃₃ | —SO₂NHCH₃ | 3-(methoxycarbonyl)-quinazolin-4(3H)-on-3-yl | 102 |
| 43 | 2,5-dimethoxyphenyl | —OC₁₆H₃₃ | —SO₂NHCH₃ | 3-(methoxycarbonyl)-quinazolin-4(3H)-on-3-yl | 95–98 |
| 44 | 4-methoxyphenyl | —OCH₃ | —NHCO—(CH₂)₃—O—(3,4-di-t-C₅H₁₁-phenyl) | 3-(methoxycarbonyl)-quinazolin-4(3H)-on-3-yl | 173–177 |

Table 4

$$\text{B-CO-CH(X)-CO-NH-} \underset{R''}{\overset{R'}{\text{C}_6\text{H}_3}}$$

| No. | B | R' | R'' | X | m.p. °C |
|---|---|---|---|---|---|
| 45 | OC₁₆H₃₃ | —OCH₃ | —COOCH₃ | benzotriazin-4(3H)-on-3-yl | 102–105 |
| 46 | t-butyl | —OC₁₆H₃₃ | —SO₂N(CH₃)₂ | benzotriazin-4(3H)-on-3-yl | 48–50 |
| 47 | t-butyl | Cl | —OC₁₆H₃₃ | benzotriazin-4(3H)-on-3-yl | 104–106 |

Table 4-continued
B—CO—CH(X)—CO—NH—C₆H₃(R')(R")
| No. | B | R' | R" | X | m.p. °C |
|---|---|---|---|---|---|
| 48 | t-butyl | Cl | —OC$_{16}$H$_{33}$ | 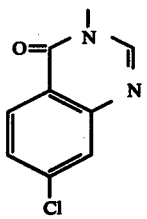 4-chloro-quinazolin-3(4H)-yl-carbonyl | 87 |
| 49 | t-butyl | —OC$_{16}$H$_{33}$ | —SO$_2$N(CH$_3$)$_2$ | 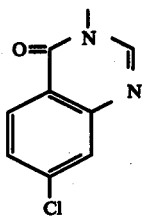 | 123 |
| 50 | t-butyl | —OC$_{16}$H$_{33}$ | —SO$_2$N(CH$_3$)$_2$ | 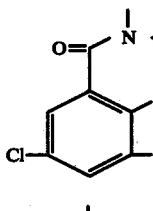 | 80 |
| 51 | t-butyl | —OC$_{16}$H$_{33}$ | —SO$_2$N(CH$_3$)$_2$ | 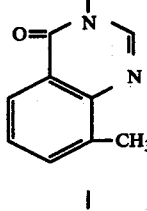 | 82 |
| 52 | t-butyl | Cl | —OC$_{16}$H$_{33}$ | 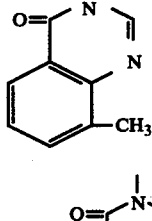 | 62 |
| 53 | t-butyl | Cl | —OC$_{16}$H$_{33}$ | 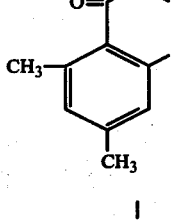 | 107 |
| 54 | t-butyl | —OC$_{16}$H$_{33}$ | —SO$_2$N(CH$_3$)$_2$ | 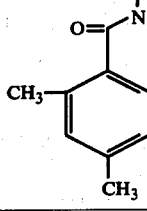 | 165 |

Table 5

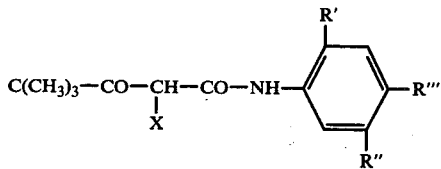

| No. | R' | R'' | R''' | X | m.p. °C |
|-----|-----|-----|------|---|---------|
| 55 | —OC$_2$H$_5$ | —OC$_2$H$_5$ | —NHCOOCHCH$_3$ 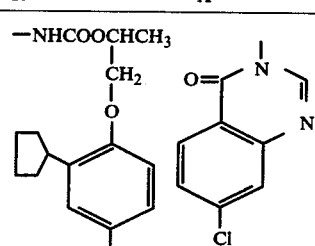 | 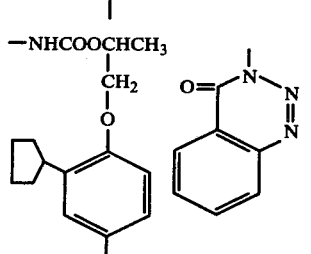 | 111–112 |
| 56 | —OC$_2$H$_5$ | —OC$_2$H$_5$ | —NHCOOCHCH$_3$ 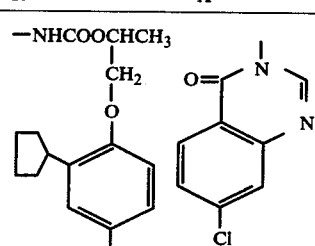 | 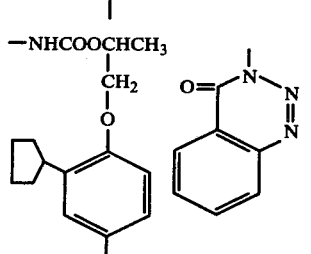 | 88–90 |
| 57 | Cl | Cl | —OC$_{14}$H$_{29}$ | 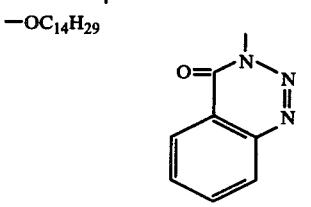 | 48–54 |
| 58 | Cl | —OC$_{14}$H$_{29}$ | Cl | 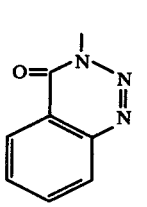 | |

The yellow couplers of this invention may be produced in a conventional manner by reaction of the corresponding 2-equivalent couplers having chlorine as their splittable substituent, with the corresponding heterocyclic compound in the presence of a base, as is described, for example, in German Offenlegungsschrift No. 2 213 461. The reaction can take place in an aprotic solvent, preferably a polar solvent, such as, for example, acetonitrile or dimethyl formamide, and with the use of suitable bases, such as aliphatic amines, e.g. triethylamine; basic heterocyclic compounds, e.g. pyridine; or alkali salts of alcoholates, e.g. sodium alcoholate. The reaction is also particularly successful in the presence of hexamethyl phosphoric acid triamide as solvent as described in German Offenlegungsschrift No. 2 329 587.

The heterocyclic compounds required for the said reaction can be prepared by known methods. 1,2,3-benzotriazinone is produced by dehydration of o-diazobenzo amides. The substituted quinazolinone-4 can be produced by reaction of substituted o-amino benzoic acid compounds with formamide or with acetamide. The reaction conditions of these reactions are well known and need not therefore be described here.

The preparation of several couplers used in this invention is described below:

Preparation of Coupler No. 5

6.0 g benzo triazinone are dissolved in a mixture of 100 ml acetonitrile and 100 ml dimethylformamid whilst stirring, and then 20 g 2,4-dimethoxybenzoyl-α-chloro-(2'-cetyloxy-5'-sulfonic methyl amide)-acetanilide and 2,2 g sodium methylat are added. The reaction mixture is heated for four hours at 70° C. Subsequently it is filtered and the solution is stirred into iced water containing hydrochloric acid. After the precipitate has been sucked off, the reaction product is dissolved in hot isopropanol, clarified with active charcoal, cooled and the supernatant solution decanted off. The residue is then purified with petroleum ether.

Yield: 14 g of coupler No. 5.

Preparation of Coupler No. 19

3.6 g 7-chloro-4-quinazolinone, 12 g α-pivaloyl-αchloro(2-cetyloxy-5-sulfonic methylamide)-acetanilide and 3.4 ml of a 30% sodium methylate solution are dissolved in 100 ml acetonitrile and boiled for 2 hours in a reflux condenser. After evaporating the solvents, the residue is stirred with methanol and the resulting product is recrystallized from methanol. Yield: 8 g of coupler No. 19.

The preparation of the other couplers used in this invention can be carried out by analogous methods.

As regards those yellow couplers in this invention which are diffusionfast, they are extremely emulsifiable, very resistant to digestion in the coating solution and in the photographic material and do not impair the photograhic properties of the emulsion, even under extreme conditions of storage.

By the preparation of the light-sensitive color materials according to the present invention diffusionfast yellow couplers of the above general formula can be incorporated into the casting composition of a silver halide emulsion or other colloidal layers which are in water-permeable relation thereto by any known means. For example, the water-soluble color couplers, i.e. those containing one or several water-soluble groups such as a sulfo or carboxyl group (as an acid or salt,) can be incorporated into the casting composition of the specific layer from an aqueous solution. Similarly, color couplers which are not or which are insufficiently water-soluble are incorporated from a solution to, respectively, suitable water-miscible or non-water-miscible, high-boiling or low-boiling organic solvents or mixtures thereof. Thereupon, the solution obtained is dispersed in a hydrophilic colloidal composition (using, if necessary, a wetting or a dispersing agent) which forms either the whole or simply a part of the binding agent of the colloidal layer. Moreover, the hydrophilic colloidal composition may contain any other type of ingredient besides the colloid. The non-water-soluble color couplers which contain fluoro-sulfonyl groups or carboxylic acid ester groups such as ethoxy carbonyl groups may also be converted by alkaline hydrolysis into the corresponding sulfonic acids or carbooxylic acids respectively, which in turn can be incorporated into hydrophilic colloidal compositions in the form of their alkali metal salts from aqueous solutions.

The solution of the color couplers does not need to be directly dispersed or dissolved in the casting composition of silver halide emulsion or some other water-permeable layer. The solution may advantageously first be dispersed or dissolved in an aqueous light-sensitive solution of a hydrophilic colloid; subsequently, the mixture obtained is thoroughly mixed with the casting composition of the light-sensitive silver halide emulsion or other water-permeable layer just before casting (after removal of the organic solvent used). Further details about particularly suitable techniques for the incorporation of color couplers into the hydrophilic colloidal layers of photographic materials may be found in the Dutch Patent Application Nos. 6 516 423, 6 516 424, 6 600 098, 6 600 099 and 6 600 628, in the Belgian Patent Specification No. 750 889, in the U.S. Pat. No. 2,304,940 and in the British Patent Specification No. 791 219.

To produce photographic color images, an exposed layer of silver halide emulsion is developed with an aromatic primary amino-developer in the presence of a color coupler according to the invention. The developer substances used may be any color developer able to yield azomethine dyes by chromogenic development. Suitable substances are aromatic compounds, such as p-phenylene diamine and its derivatives, for example N,N-dialkyl-p-phenylenediamine as exemplified by N,N-diethyl-p-phenylenediamine, N,N-dialkyl-N'-sulfomethylp-phenylenediamine and N,N,-dialkyl-N'-carboxymethyl-p-phenylenediamine.

Suitable light-sensitive emulsions are emulsions of silver halides, such as silver chloride, silver bromide or mixtures thereof which may have a small content of silver iodide up to 10 Mols-%, in one of the hydrophilic binding agents normally used. Gelatin is the preferred binding agent for the photographic layers. This can, however, be replaced wholly or in part by other natural or synthetic binding agents. Suitable natural binding agents are e.g. alginic acid and its derivatives such as salts, esters or amides; cellulose derivatives such as carboxymethylcellulose; alkylcellulose and hydroxyethylcellulose; starch or its derivatives such as ethers or esters; or carageenates. Among the synthetic binding agents, polyvinylalcohol, partially saponified polyvinylacetate, polyvinylpyrrolidone and the like should be mentioned.

The emulsions may also be chemically sensitized, e.g. by the addition of sulfur-containing compounds during chemical ripening, for example, allylisothiocyanate, allylthiourea and sodiumthiosulfate. Furthermore, reducing agents such as, for example, the tin compounds described in Belgian Patent Specification Nos. 493 464 or 568 687, as well as polyamines such as diethylenetriamine or aminomethane sulfinic acid derivatives (as in Belgian Patent Specification 547 323) may also be used as chemical sensitizers. In addition, the rare metals such as gold, platinum, palladium, iridium, ruthenium or rhodium are suitable as chemical sensitizers. This method of chemical sensitization has been described in the article by R. KOSLOWSKY, Z. Wiss. Phot., Vol. 46, 65–72, (1951).

It is also possible to sensitize the emulsions with polyalkyleneoxide derivatives, e.g. with polyethylene oxide having a molecular weight of from 1,000 to 20,000, and further with the condensation products of alkylene oxides and aliphatic alcohols, glycols, cyclic dehydration products of hexitoles; with alkyl-substituted phenols, aliphatic carboxylic acids, aliphatic amines, aliphatic diamines and amides.

The condensation products have a molecular weight of at least 700, preferably of more than 1000. To obtain special effects, the sensitizers can, of course, be combined, in the manner described in Belgian Patent Specification No. 537 278 and in British Patent Specification No. 727 982.

The emulsions must exhibit sufficient sensitivity in the blue region of the spectrum. For this, unsensitized emulsions are generally used, their sensitivity depending on that of the specific silver halide used. It is, however, also possible to sensitize the silver halide emulsions in the blue region of the spectrum, e.g. by sensitizers such as are described in the British Patent Specification No. 1 285 078.

The emulsions can contain conventional stabilizers, e.g. homopolar or salt-like compounds of mercury with aromatic or heterocyclic rings, such as mercaptotriazoles, simple mercuric salts, sulfonium mercuric double salts and other mercury compounds. Other suitable stabilizers are azaindenes, preferably tetra- and pentazaindenes, especially those which are substituted with hydroxyl or amino groups. Such compounds have been described in the articles by BIRR, Z. Wiss. Phot., Vol. 47, 2-58 (1952). Other suitble stabilizers are heterocyclic mercapto compounds, e.g. phenylmercaptotetrazole, quaternary benzothiazole derivatives and benzotriazole.

The emulsions can be hardened in the usual manner, for example with formaldehyde or with halogen-substituted aldehydes containing a carboxyl group such as mucobromic acid, diketones, methane sulfonic acid ester and dialdehydes.

The following examples illustrate the advantages of the couplers of this invention:

EXAMPLE 1

2 mMol of the couplers (formula given below) were each dissolved in 3 ml ethyl acetate and, after adding 0.5 g dibutylphthalate emulsified with 20 ml of a 5% gelatin solution at 60° C. To the emulsion is added 0.16 g sodium dodecylbenzene sulfonate.

Subsequently the emulsion was mixed with 85 g of a 7.5% gelatin solution, containing 1.93 g dispersed silver bromide, and then diluted with water until the casting viscosity is reached.

After casting the emulsion onto a transparent support of cellulose triacetate, the material thus produced is exposed behind a grey step wedge and cut into several test samples.

One set of test samples was stored for 7 days at 57° C. and 34% relative humidity in a heating cupboard before being photographically processed. Another set of test samples was immediately processed by developing for 2 minutes, and a third set of test samples for 8 minutes, in a conventional color developer both containing N,N-diethyl-p-phenylene-diamine as developer, and are then bleached and fixed as usual. The stored, i.e. first set of test samples, are processed in the same way by developing for 8 minutes. All test samples then are sensitometrically evaluated.

The couplers used are of the following formula:

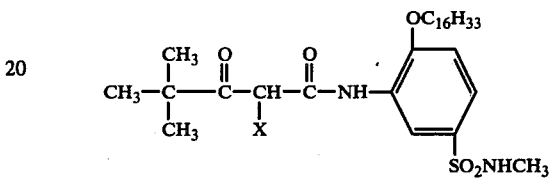

where X is as defined in Table 6.

Table 6

| Coupler | X | S | Sensitivity DIN | $D_{max}$ 2 min | $D_{max}$ 8 min | ΔS |
|---|---|---|---|---|---|---|
| A according to GB 980,507 | H | 0.06 | ± 0 | 0.8 | 2.0 | + 0.03 |
| B according to GB 980,507 | Cl | 0.16 | + 5.0 | 1.0 | 2.9 | + 0.03 |
| C according to DT-OS 2,318,807 | (pyridinone) | 0.07 | + 2.7 | 1.1 | 2.7 | + 0.06 |
| D according to GB 1,331,179 | (phthalimide) | 0.07 | + 7.3 | 1.9 | 2.9 | + 0.16 |
| E | (hydroxypyridazinone) | 0.07 | + 5.3 | 1.3 | 2.8 | + 0.05 |
| F | (hydroxypyridinone) | 0.09 | + 3.3 | 1.6 | 2.8 | + 0.05 |
| G | (benzoxazinone) | 0.06 | + 5.3 | 1.3 | 2.9 | + 0.07 |

Table 6-continued

| Coupler | X | S | Sensitivity DIN | $D_{max}$ 2 min | $D_{max}$ 8 min | ΔS |
|---|---|---|---|---|---|---|
| 2 | 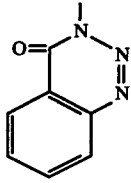 | 0.07 | + 7.0 | 1.7 | 2.9 | + 0.08 |

The sensitometric evaluation of the individual test samples is also shown in Table 6 which gives a comparison of the basic fog values (S) obtained with those test samples developed for 8 minutes; the increase in basic fog values (ΔS) between the test samples stored in the heating cupboard before being developed and the unstored test samples, the relative sensitivity in DIN units, and the maximum densities produced ($D_{max}$).

As can be seen from Table 6, the coupler 2 of the present invention produces dyes with unusually high sensitivity as well as very high density and with an acceptable amount of fog.

The reference coupler D is adversely affected in stability during warm and moist storage so that a considerable increase in the fog value ΔS can be observed.

Compared with coupler C (described in the German Offenlegungsschrift DT-OS No. 2,318,807) the yellow coupler 2 of this invention is remarkable on account of its greater sensitivity as well as its higher rate of reaction.

EXAMPLE 2

Sets of test samples of photographic material containing coupler No. 5, were produced and tested as described in Example 1 above, but without the 2-minute development test.

The following results were obtained:

| Coupler | X | S | Sensitivity | $D_{max}$ | ΔS |
|---|---|---|---|---|---|
| 5 | 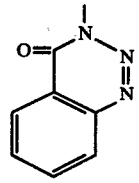 | 0.07 | + 6.3 | 2.9 | + 0.05 |

A comparison of these values with the corresponding values of the yellow coupler 2 of the present invention in Table 6 shows that benzoylacetanilide yellow couplers also exhibit extremely good properties as regards reactivity, sensitivity and stability during storage.

EXAMPLE 3

2 mMol of the couplers (formula given below) were each added to photographic emulsions and photographic materials prepared as described in Example 1.

In contrast to Example 1 the photographic materials were then exposed while still wet and after cutting into several test samples one set of the test samples was stored for 7 days at 57° C. and 34% relative humidity in a heating cupboard before being photographically processed.

Another set of test samples was immediately processed by developing for 2 minutes and a third set of test samples for 8 minutes in an conventional color developer containing N,N-diethyl-p-phenylene-diamine as developer and are then bleached and fixed as usual.

The stored, i.e., the first set of test samples are processed in the same way by developing for 8 minutes. All test samples are then sensitometrically evaluated.

The couplers used are of the formula shown in Example 1 wherein X is defined in Table 7.

Table 7

| | X | S | Sensitivity DIN | $D_{max}$ 2Min | $D_{max}$ 8Min | ΔS |
|---|---|---|---|---|---|---|
| A according to GB 980,507 | H | 0.06 | ± 0 | 0.8 | 2.0 | +0.06 |
| B according to GB 980,507 | Cl | 0.16 | +5.0 | 1.0 | 2.9 | +0.36 |
| C according to DOS 2 318 807 | 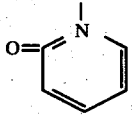 | 0.07 | +2.7 | 1.1 | 2.7 | +0.09 |

Table 7-continued

| X | | S | Sensitivity DIN | $D_{max}$ 2Min | $D_{max}$ 8Min | ΔS |
|---|---|---|---|---|---|---|
| D according to GB 1 331 179 | 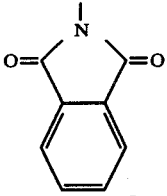 | 0.12 | +7.3 | 1.9 | 2.9 | +1.20 |
| G | 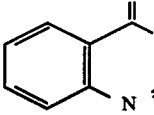 | 0.08 | +5.3 | 1.3 | 2.9 | +0.16 |
| 2 | 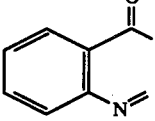 | 0.10 | +7.0 | 1.3 | 2.9 | +0.18 |
| 19 | 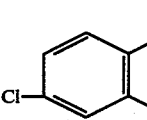 | 0.08 | +7.7 | 1.6 | 3.1 | +0.18 |
| 26 | 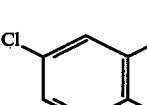 | 0.08 | +6.3 | 1.7 | 3.0 | +0.14 |
| 28 | 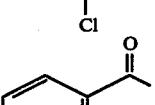 | 0.10 | +5.7 | 1.7 | 2.7 | +0.20 |
| 33 | 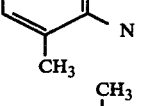 | 0.08 | +7.0 | 1.4 | 2.8 | +0.18 |

The sensitometric evaluation of the individual test was performed as described in Example 1.

As can be seen from Table 7, the couplers of the present invention produce dyes with unusually high sensitivity as well as very high density with an acceptable amount of fog. The couplers of the invention are further in particular remarkable on account of their greater sensitivity as well as their advantageous stability on storage in the heating cupboard which is expressed in the very suitable low increase of the fogging values. (ΔS).

Obviously many modifications and variations of the present invention are possible in the light of the above teachings. It is, therefore, to be understood that within the scope of the appended claims the invention may be practiced otherwise than as specifically described.

What is claimed:

1. In a light-sensitive material having a silver halide emulsion layer in effective contact with a 2-equivalent yellow coupler carrying a nitrogen-containing 6-membered heterocycle connected by said nitrogen atom to the coupling position of an open-chain ketomethylene yellow coupler and having a carbonyl carbon adjacent said nitrogen, which heterocycle splits off during coupling, the improvement according to which said heterocycle is

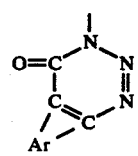

in which Ar is a carbocyclic aromatic ring fused to the two carbons to which it is connected.

2. The combination of claim 1 in which the aromatic ring is selected from the class consisting of an unsubstituted ring and a ring that is substituted with methyl or nitro groups.

3. The combination of claim 2 in which the coupler is a pivaloyl acetanilide coupler.

4. The combination of claim 2 in which the coupler is a benzoyl acetanilide coupler.

5. In a light-sensitive silver halide emulsion containing a 2-equivalent yellow coupler, the improvement according to which the coupler is a diffusion-fast pivaloylacetanilide coupler substituted in its coupling position by the group

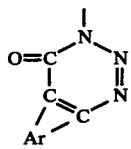

in which Ar is an unsubstituted carbocyclic aromatic ring fused to the two carbons to which it is connected.

6. In a photographic material comprising a light sensitive silver halide emulsion layer and a yellow color coupler in reactive association with the said silver halide emulsion layer, wherein the improvement comprises said coupler being an open-chain ketomethylene yellow coupler having attached to its methylene coupling position a 1, 2, 3-benzotriazine-4-(3H)-one heterocyclic nucleus.

7. In a light-sensitive material having a silver halide emulsion layer in effective contact with a 2-equivalent yellow coupler carrying a photographically relatively inert nitrogen-containing 6-membered heterocycle connected by said nitrogen atom to the coupling position of an open-chain ketomethylene yellow coupler and having a carbonyl carbon adjacent said nitrogen, which heterocycle splits off during coupling, the improvement according to which said heterocycle is a 1,3-quinazolinone-4 in which said nitrogen is the nitrogen in the 3-position, and in at least one of the 2,5,6,7 and 8 positions there is a carboxy, alkoxycarbonyl having up to 5 carbon atoms, nitro, methyl or chloro substituent.

8. The combination of claim 7 in which the coupler is a pivaloyl acetanilide coupler.

9. The combination of claim 7 in which the coupler is a benzoyl acetanilide coupler.

* * * * *